United States Patent [19]

Lee

[11] Patent Number: 4,596,553
[45] Date of Patent: Jun. 24, 1986

[54] METHOD AND APPARATUS FOR PERFORMING SUCTION LIPECTOMY

[76] Inventor: Hans Lee, Suite 200, 415 Morris St., Charleston, W. Va. 25301

[21] Appl. No.: 607,714

[22] Filed: May 7, 1984

[51] Int. Cl.⁴ .................................... A61M 31/00
[52] U.S. Cl. ............................ 604/49; 604/117
[58] Field of Search .............. 604/49, 51, 73, 19, 604/21, 117

[56] References Cited

U.S. PATENT DOCUMENTS

| | | | |
|---|---|---|---|
| 390,177 | 9/1888 | Lee | 604/280 |
| 504,352 | 9/1893 | Heysinger | 30/286 |
| 1,698,331 | 1/1929 | Gunter | 433/94 |
| 1,749,919 | 3/1930 | Mierley | 128/305 |
| 2,198,666 | 4/1940 | Gruskin | 128/215 |
| 2,338,800 | 1/1944 | Burke | 604/117 |
| 2,545,115 | 3/1951 | Son | 128/215 |
| 2,705,949 | 4/1955 | Silverman | 604/117 X |
| 2,715,899 | 8/1955 | MacLean | 418/159 |
| 2,876,539 | 7/1954 | Ford | 30/283 |
| 3,920,001 | 11/1975 | Edwards | 128/765 |
| 4,235,234 | 11/1980 | Whitney et al. | 607/117 |
| 4,318,414 | 3/1982 | Schuster et al. | 128/759 |
| 4,536,180 | 8/1985 | Johnson | 604/268 |

*Primary Examiner*—Ferris H. Lander
*Attorney, Agent, or Firm*—Lowe, King, Price & Becker

[57] ABSTRACT

A cannula is provided with a guide bar extending in spaced, parallel relationship to the cannula. Adjacent and overlying a hole formed in the cannula tip through which suction is applied to surgically aspirate fatty tissue is a guide surface adapted to contact and slide against the skin of a patient while the cannula tip is manually directed by the surgeon through the fatty tissue in reciprocating strokes. The guide surface maintains the tip at a constant depth within the tissue so that, upon completion of suction lipectomy, a desired amount of fatty tissue is surgically aspirated while leaving an even thickness layer of tissue intact. A new surgical procedure for performing suction lipectomies with the guided cannula of the invention is also disclosed.

11 Claims, 9 Drawing Figures

U.S. Patent   Jun. 24, 1986   4,596,553
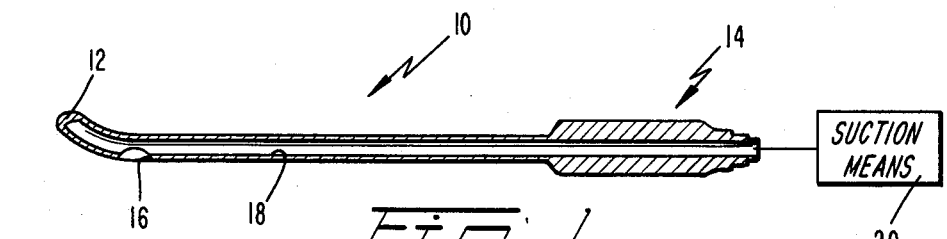
Fig. 1
PRIOR ART
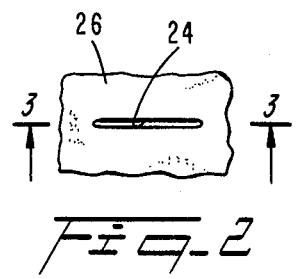
Fig. 2
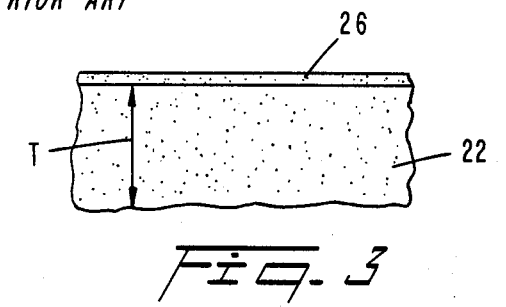
Fig. 3
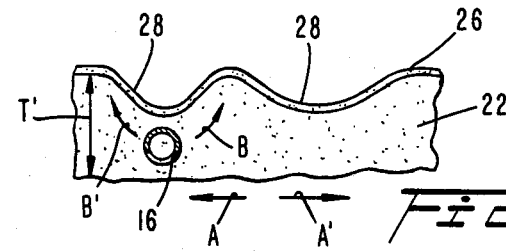
Fig. 3A
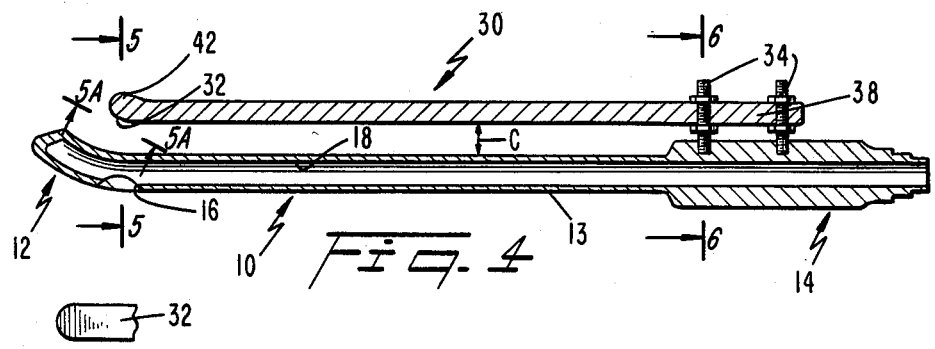
Fig. 4
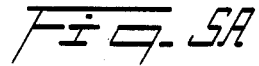
Fig. 5A
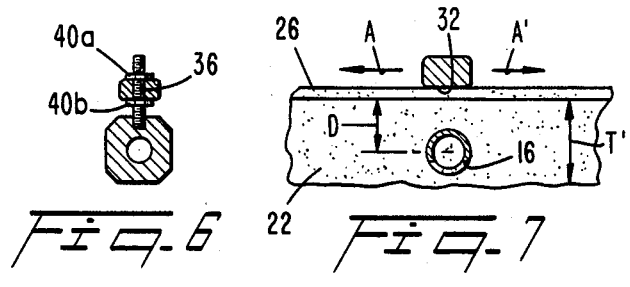
Fig. 6   Fig. 7
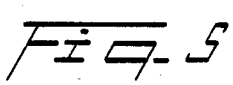
Fig. 5

METHOD AND APPARATUS FOR PERFORMING SUCTION LIPECTOMY

TECHNICAL FIELD

The present invention relates generally to surgical instruments and, more particularly, to a surgical cannula and its method of use in performing suction lipectomy to remove excessive accumulations of fatty tissue from a human body.

BACKGROUND ART

Suction lipectomy or lipolysis is a surgical procedure for removing fatty tissue and fatty tumors from localized areas of the human body through small incisions that can be easily concealed. The surgical procedure customarily employed requires an incision in the skin to expose the fatty tissue. The tip of a cannula is then inserted into the incision and manually directed by the surgeon towards the desired area of the body. By guiding the tip through the fatty tissue while simultaneously applying suction through a longitudinal passage extending through the cannula in communication with the tip, fat is surgically aspirated from the body. For adequate aspiration, approximately 15-20 strokes of the tip through the fatty tissue are often necessary.

FIG. 1 is an illustration of a conventional cannula 10 used for suction lipectomy having a tip 12 and a handle 14 formed at opposite ends thereof. Tip 10 has a hole 16 communicating with a central longitudinal passage 18 extending through the cannula for connection to a suction means 20 in a well known manner. To remove a desired amount of fat from fatty tissue 22 (see FIGS. 2 and 3), an incision 24 is first made in skin 26 to expose the tissue. Tip 10 is then inserted through incision 24 into tissue 26. By gripping handle 14 to move tip 12 through the fatty tissue in continuous reciprocating strokes (see arrows A and while A') applying suction, fat is surgically aspirated throug hole 16 and passage 18. After a sufficient number of strokes by the surgeon, the original thickness T of fatty tissue is reduced to a lesser thickness T' (see FIG. 3A).

Because suction lipectomy is essentially cosmetic surgery, considerable surgical skill is necessary to repetitively guide tip 12 in directions A, A' to leave an even layer of tissue intact. This requires guiding tip 12 at a constant depth beneath the skin. Otherwise, different thicknesses of remaining tissue will cause permanent indentations 28 to appear in the skin following surgery (see FIG. 3A), which can be very unsightly. Unfortunately, however, the results frequently obtained with suction lipectomy are of the type shown in FIG. 3A, since the surgeon does not always know or cannot maintain the precise depth at which he guides tip 12 through the tissue. Further, since the surgeon must guide the tip in directions A, A', there is a tendency during the stroke to rotate the cannula about its longitudinal axis, causing hole 16 to move above or below the desired depth. Even if the surgeon possesses sufficient skill to guide tip 12 at constant depth, the large number of repetitive strokes necessary for adequate aspiration renders the surgical procedure fatiguing to the surgeon, possibly resulting in momentary loss of control while guiding the cannula.

It is equally important that the surgeon avoid excessive penetration of the cannular tip through the fatty tissue; otherwise damage to vital organs can occur.

It is accordingly an object of the present invention to provide an improved cannula that is easily guided by the surgeon at a constant depth so that a desired amount of fatty tissue is surgically aspirated while leaving an even thickness layer of tissue intact.

Another object is to provide an improved surgical procedure for performing suction lipectomy so that a desired amount of fatty tissue is surgically aspirated while leaving an even thickness layer of tissue intact.

Still another object is to provide an improved cannula that facilitates maneuverability and controllability thereof by the surgeon during surgical aspiration.

Yet a further object is to provide a cannula that is easy for the surgeon to manipulate, rendering lipolysis less fatiguing to the surgeon to improve safety.

A further object is to provide a cannula that is simple in design and economical to manufacture.

Still another object is to provide a cannula having means preventing excessive penetration of the cannula tip into the body, avoiding possible damage to vital organs.

DISCLOSURE OF THE INVENTION

A device for surgically aspirating subcutaneous fatty tissue from an animate body, in accordance with the invention, comprises a cannula having a tip and a handle at opposite ends thereof. The tip is formed with a hole. A longitudinal passage extends through the cannula in communication with the hole. The passage is connectible to a source of vacuum so that suction can be applied to surgically aspirate fatty tissue through the hole when the tip is implanted in tissue. A guide bar is attached to the cannula for maintaining the hole at a predetermined desired depth within the tissue as the tip is manually directed by a surgeon.

The guide bar is preferably an elongate member having one end connected to a portion of the cannula remote from the tip and an opposite, free end terminating adjacent the hole in spaced relationship to the tip. The opposite end has a guide surface facing the cannula. During surgery, this guide surface contacts the skin surface overlying the fatty tissue to control the depth at which the tip removes fat so that an even thickness layer of tissue remains intact upon completion of surgery.

In accordance with another aspect of the invention, the free end of the guide bar is of similar curvature as the tip. The guide bar is preferably of rectangular cross section having rounded edges and rounded corners for safe contact with the surgeon's hands. The guide surface is generally rectangular in plan view and fully contacts the skin to resist excessive penetration of the tip through the tissue as well as minimize the tendency of the tip to pivot or rotate out of the predetermined depth.

In accordance with yet another aspect of the invention, the guide bar is preferably connected to the cannula handle by means of a pair of longitudinally spaced bolts extending respectively through holes formed in one end of the guide bar remote from the guide surface. The bolts pass through holes formed in the guide bar in sliding contact therewith. A pair of nuts threaded onto each bolt contact opposite sides of the guide bar to retain same in spaced location from the cannula. The nuts are adjustable to vary the spacing between the guide surface and cannula tip to achieve a desired degree of penetration into fatty tissue.

A method of surgically aspirating subcutaneous fatty tissue from desired areas of an animate body with a cannula is also disclosed. The cannula has a tip and a handle at opposite ends thereof. The tip is formed with a hole and a longitudinal passage extends through the cannula in communication with the hole. The passage is connected to a vacuum source so that suction is applied through the hole. The cannula further includes a guide member having a surface spaced from the tip. In accordance with the method of the present invention, an incision is formed in the skin to expose the subcutaneous fatty tissue. The tip of the cannula is inserted by the surgeon through the incision so that the hole contacts the fatty tissue and the guide surface rests on the skin. Suction is applied through the hole while simultaneously moving the tip through the tissue in reciprocating strokes to surgically aspirate tissue in contact with the hole. The hole is guided within the tissue at a constant predetermined depth by maintaining the guide surface in contact with the skin while moving the tip through the tissue in reciprocating strokes.

In accordance with another aspect of the method of the invention, lubricant can be applied to portions of the skin engageable with the guide surface to reduce friction therebetween, thereby facilitating surgical aspiration.

Still other objects of the present invention will become readily apparent to those skilled in this art from the following description wherein there is shown and described a preferred embodiment of this invention simply by way of illustration of one of the best modes contemplated for carrying out the invention. As will be realized, the invention is capable of other different embodiments, and its several details are capable of modifications in various, obvious respects, all without departing from the invention. Accordingly, the drawing and description will be regarded as illustrative in nature and not as restrictive.

BRIEF DESCRIPTION OF THE DRAWING

The accompanying drawings incorporated in and forming a part of the specification, illustrate several aspects of the present invention, and together with the description serve to explain the principles of the invention. In the drawings:

FIG. 1 is a side elevational view of a conventional cannula commonly used to perform suction lipectomies;

FIG. 2 is a top view of an area of the body on which suction lipectomy is to be performed through an incision formed in the skin;

FIG. 3 is an enlarged fragmentary sectional view taken along the line 3—3 of FIG. 2 showing the tip of the prior art cannula of FIG. 1 inserted into the fatty tissue through the incision prior to surgical aspiration;

FIG. 3A is a view similar to FIG. 3 showing typical results obtained with the prior art cannula of FIG. 1 upon completion of the suction lipectomy;

FIG. 4 is a side elevational view of the cannula in accordance with the present invention;

FIGS. 5 and 5A are sectional views taken respectively along the lines 5—5 and 5A—5A of FIG. 4 showing the positional relationship of the guide bar relative to the suction hole of the cannula and a plan view of the guide surface;

FIG. 6 is a sectional view taken along the line 6—6 of FIG. 4 of a mechanism for connecting as well as adjusting the spacing between the cannula and guide bar; and FIG. 7 is a view similar to FIG. 3A but showing the results of suction lipectomy obtained with the cannula of the present invention.

BEST MODE FOR CARRYING OUT THE INVENTION

A conventional cannula 10 used for suction lipectomy, as mentioned briefly above, has a tip 12 and a handle 14 formed at opposite ends of an elongate, straight tubular section 13. Tip 12 is inclined upward from straight section 13 at an angle of about 30°. A suction hole 16 in communication with passage 1 formed in the cannula wall at a region where straight section 13 merges into tip 12.

In conventional use, handle 14 is held by the surgeon and cannula tip 12 is inserted through incision 24 and moved beneath skin 24 through subcutaneous tissue 22 in reciprocating strokes. Suction hole 16 is the lowermost point at which cannula 10 penetrates tissue 22. Tip 12 projects upward from hole 16 and is spaced about $\frac{1}{2}''-1\frac{1}{2}''$ therefrom to act as a stop preventing undesirable aspiration of fatty tissue in contact with the patient's skin.

As discussed briefly above, since repetitive strokes are necessary to surgically aspirate fat within a particular region of the body proximate incision 24, suction lipectomy is often a long, arduous procedure for the surgeon who, to obtain satisfactory results, must guide and maintain tip 12 at a constant depth by grasping handle 14 with a single hand. During this tedious procedure, handle 14 is often inadvertently rotated by the surgeon during the aforesaid reciprocation of the cannula, causing hole 16 to rotate (in directions B or B') about tip 12 out of desired depth D. Too, since hole is solely (and blindly) maintained at desired depth D by surgical skill, fatigue and relative surgical inexperience often results in the surgeon allowing the cannula hole to stray out of depth D. In either case, an uneven thickness layer of fatty tissue remaining intact after surgery causes the skin to have an unsightly, wavy appearance, as shown in FIG. 3A.

In accordance with the present invention, cannula 10 includes a guide bar 30 having a guide surface 32 pressed by the surgeon into constant contact with skin 24 so that suction hole 16 remains at constant depth during reciprocation of the cannula. The guide bar 30 is an elongate member of rectangular cross section preferably formed of medical grade stainless steel. As best shown in FIGS. 4 and 6, guide bar 30 extends in spaced, parallel relationship with cannula 10 and is connected to the cannula by means of a pair of threaded bolts 34 secured to handle 14. Bolts 34 respectively pass through longitudinally spaced through holes 36 formed at one end 38 of bar 30 overlying the handle. The diameter of through holes 36 is larger than the external threaded diameter of bolts 34, enabling the guide bar to slide on the bolts to vary the spacing between the guide and cannula as discussed more fully below.

To secure guide bar 30 to cannula 10 at a constant spacing C, a pair of nuts 40a and 40b are threaded onto each bolt 34 to respectively contact opposite surfaces of bar 30. With this arrangement, bar 30 can be securely tighten into a fixed position relative to cannula 10 by tightening nuts 40A, 40B against end 38. To adjust the spacing between the cannula and guide bar, one of nuts 40A, 40B on each bolt 34 is loosened, enabling the bar to slide on the bolt. Thereafter, the other nut is tightened against the repositioned bar to lock same into the adjusted position.

Guide surface 32, as best illustrated in FIGS. 4 and 5A, is formed at the free end 42 of guide bar 30. The free end 42 is inclined upward from bar 30 to approximate the curvature of tip 12 and terminates short of the tip so that surface 32 overlies and is generally parallel to the mouth of cannula hole 16. In use, the guide surface 32 is positioned to rest upon skin 26 so that the cannula hole is embedded in tissue 22 at a predetermined desired depth C determined by the aforesaid nut and bolt arrangement. As best shown in FIG. 7, the hole 16 is maintained at constant depth by the surgeon during reciprocating movement of the cannula by virtue of guide surface 32 being easily pressed in sliding contact with the skin. Thus, upon completion of the suction lipectomy, a uniform thickness layer T' (T' is less than original thickness T) remains intact so that skin 24 has an even, pleasing appearance.

Since cannula tip 10 is introduced into tissue 22 through incision 24 at an angle (not shown in detail), the guide surface 32 is easily positioned on the surface of skin 26 in overlying relation to cannula hole 16. Since the guide surface is preferably smooth and rectangular in area (FIG. 5A), this smooth surface establishes a stable base that easily moves along the skin and resists any leveraging action tending to be imparted by the surgeon to the cannula tip during movement of handle 14. Thus, by applying a gentle downward pressure to ensure contact between surface 32 and skin 26, the guide surface provides a visual point of reference for the surgeon so that the cannula hole surgically aspirates fat at a constant depth.

The provision of guide surface 32 allows the surgeon to utilize both hands in gripping handle 14 to move cannula 10. Thus, the surgical procedure is less fatiguing to the surgeon.

To ensure that guide surface 32 slides smoothly along the surface of skin 26, a lubricant is preferably applied to the skin to reduce friction.

The foregoing description of the preferred embodiment of the invention has been presented for purposes of illustration and description. It is not intended to be exhaustive or to limit the invention to the precise form disclosed, and obviously many modifications and variations are possible in light of the above teaching. For example, the present invention can be practiced with cannulas formed with plural suction holes. Also holes can be located not only facing downward but also sideway (both) to facilitate more even aspiration. Since overlying guard prevents rotation of cannula side holes will not aspirate superficial fatty tissue. Additionally, tip 12 need not necessarily be curved upward as discussed above; the cannula tip can be straight or curved downward, to accommodate different areas (or contours) of the body on which suction lipectomy is to be performed. However, for best results, free end 42 (i.e., surface 32 of guide 30 is always parallel (i.e., of similar curvature) to the cannula tip. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Fixation (spacing) mechanism of cannula and guard can be modified such as hinge mechanism for proximal bolt (away from tip) and larger and round nuts with roughened rim for distal bolt (closer to tip). This modification will simplify spacing cannula and guard manually without wrench.

I claim:

1. A device for surgically aspirating subcutaneous fatty tissue and the like from an animate body, comprising:
    (a) a cannula having a tip and a handle at opposite ends thereof, the tip being formed with a hole, and a longitudinal passage extending through the cannula in communication with the hole, said passage being connectable to a source of vacuum so that suction can be applied to surgically aspirate and remove fatty tissue through the hole when the tip is inserted in the tissue;
    (b) guide means attached to the cannula and spaced apart from said tip for maintaining the hole at a predetermined generally constant depth within the tissue as the length of said cannula and tip is manually directed by a surgeon through the tissue in reciprocating strokes with a guide surface of said guide means being in substantially constant contact with the surface of said skin overlying the fatty tissue during said strokes; and
    (c) means for connecting the guide means to the cannula.

2. The device of claim 1, wherein said guide means includes an elongate guide bar having one end connected to a portion of the cannula remote from the tip and an opposite free end terminating adjacent the hole in spaced relationship to the tip, said opposite end having said guide surface in contact with, during surgery, a portion of the skin overlying the fatty tissue to limit the depth at which the hole penetrates the tissue.

3. The device of claim 2, wherein said guide surface is generally parallel to the mouth of the hole.

4. The device of claim 2, further including means for adjusting the spacing between the guide surface and cannula to thereby enable the surgeon to select the depth at which the hole will move through the tissue relative to the guide surface.

5. The device of claim 4, wherein said adjusting means includes means for varying said spacing by an infinitely variable amount.

6. The device of claim 4, wherein said connecting means includes a pair of longitudinally spaced bolts connecting the guide bar to the handle, said bolts extending respectively through holes formed in said one end of the guide bar in sliding contact therewith, and a pair of nuts threaded onto each bolt to contact opposite sides of the guide bar, said nuts coacting to adjust and maintain a desired spacing between the guide bar and cannula.

7. The device of claim 2, wherein said guide bar is of rectangular cross section having rounded edges and rounded corners to prevent injury to the surgeon's hands and the patien skin.

8. The device of claim 7, wherein said guide surface is rectangular in plan view.

9. A method of surgically aspirating to remove subcutaneous fatty tissue from desired areas of an animate body with the cannula having a tip and a handle at opposite ends thereof, the tip being formed with a hole, and a longitudinal passage extending through the cannula in communication with the hole, said passage being connected to a vacuum source so that suction is applied through the hole, said cannula further including a guide member having a surface spaced from the tip, comprising the steps of:
(a) forming an incision to expose said subcutaneous fatty tissue;
(b) inserting the tip of the cannula through the incision so that the hole contacts the fatty tissue and the guide surface rests on the skin;
(c) applying suction through the hole while simultaneously moving the tip through the tissue in reciprocating strokes to surgically aspirate tissue in contact with the hole; and
(d) guiding the hole within the tissue at a constant predetermined depth by moving the guide surface in constant contact with the skin surface while moving the tip and the cannula through the tissue in said reciprocating strokes.

10. The method of claim 9, comprising the further step of applying a lubricant to portions of the skin engageable with the guide surface to reduce friction therebetween.

11. A device for positioning a tip of a cannula at a constant depth within subcutaneous fatty tissue to surgically aspirate the tissue upon application of suction supplied thereto through the tip, comprising guide means mounted on the cannula and spaced apart from said tip for maintaining said tip at said constant depth as the length of said cannula and tip is manually directed by a surgeon through the tissue in reciprocating strokes, said guide means including a guide surface spaced above and overlying the tip and located to remain in substantially constant contact with a portion of the skin covering the fatty tissue such that the cannula hole remains at substantially constant depth during the stroking movement; and means for connecting the guide means to the cannula.

* * * * *